United States Patent [19]
Müller et al.

[11] Patent Number: 6,106,797
[45] Date of Patent: Aug. 22, 2000

[54] GAUZE CATALYST BASED ON TITANIUM OR VANADIUM ZEOLITES AND INERT GAUZE FABRICS FOR ACCELERATING OXIDATION REACTIONS

[75] Inventors: Ulrich Müller, Neustadt; Franz Josef Bröcker, Ludwigshafen; Georg Heinrich Grosch, Dürkheim; Hermann Pütter, Neustadt; Michael Schulz, Ludwigshafen; Norbert Rieber, Mannheim; Wolfgang Harder, Weinheim, all of Germany

[73] Assignee: BASF Aktiengesellschaft, Ludwigshafen, Germany

[21] Appl. No.: 09/117,293

[22] PCT Filed: Feb. 20, 1997

[86] PCT No.: PCT/EP97/00804

§ 371 Date: Aug. 26, 1998

§ 102(e) Date: Aug. 26, 1998

[87] PCT Pub. No.: WO97/31711

PCT Pub. Date: Sep. 4, 1997

[30] Foreign Application Priority Data

Feb. 29, 1996 [DE] Germany ............ 196 07 577

[51] Int. Cl.$^7$ .................................. C01B 15/029
[52] U.S. Cl. ............... 423/584; 502/60; 502/64; 502/74; 549/531; 564/300; 564/301
[58] Field of Search .................. 502/60, 64, 74; 423/584; 549/531; 564/300, 301

[56] References Cited

U.S. PATENT DOCUMENTS 5,843,392  12/1998  Jansen et al. .
5,912,367   6/1999  Chang .
6,008,388  12/1999  Dessau et al. .

FOREIGN PATENT DOCUMENTS

| | | |
|---|---|---|
| 0 100 119 | 2/1984 | European Pat. Off. . |
| 0 208 311 | 1/1987 | European Pat. Off. . |
| 0 376 453 | 7/1990 | European Pat. Off. . |
| 0 388 094 | 9/1990 | European Pat. Off. . |
| 0 511 739 | 11/1992 | European Pat. Off. . |
| 271 101 | 8/1989 | Germany . |
| 44 25 672 | 1/1996 | Germany . |
| 2116974 | 10/1983 | United Kingdom . |

OTHER PUBLICATIONS

S. Yamazaki, et al., Microporous Materials, vol. 5, pp. 245–253, "Synthesis of a Mordenite Membrane on a Stanless–Steel Filter And Polytetrafluoroethylene Plate Substrates", Jul. 15, 1995.

Hans Peter Calis, et al., Chem.–Ing.–Tech., No. 67, No. 6, pp. 777–780, "Anwendung Von Zeolithen Bei Der Selektiven Katalytischen Reduktion Von, $No_x$ In Industrieabgasen", 1995.

*Primary Examiner*—Tom Dunn
*Assistant Examiner*—Christina Ildebrando
*Attorney, Agent, or Firm*—Oblon, Spivak, McClelland, Maier & Neustadt, P.C.

[57] ABSTRACT

The present invention relates to a gauze catalyst based on titanium or vanadium zeolites and inert gauze fabrics which is suitable for accelerating oxidation reactions such as epoxidation of olefins, hydrogen peroxide production or hydroxylamine synthesis.

11 Claims, No Drawings

GAUZE CATALYST BASED ON TITANIUM OR VANADIUM ZEOLITES AND INERT GAUZE FABRICS FOR ACCELERATING OXIDATION REACTIONS

This application is the national stage of International Application No. PCT/EP97/00804 filed Feb. 20, 1997.

The present invention relates to a gauze catalyst based on titanium or vanadium zeolites and inert gauze fabrics and its use for accelerating oxidation reactions. The present invention further relates to corresponding processes for preparing epoxides, hydrogen peroxide and hydroxylamines.

Titanium zeolites are known to be suitable for use as catalysts for oxidation reactions. For instance, EP-A 100 119 (1) discloses a process whereby propene can be epoxidated in the presence of a solvent with aqueous hydrogen peroxide to propylene oxide over titanium zeolites. The preparation of cyclohexanone oxime from cyclohexanone by reaction with ammonia and hydrogen peroxide over titanium silicalites is taught in EP-A 208 311 (2) and the hydroxylation of aromatics with hydrogen peroxide over synthetic zeolites is known from GB-A 2 116 974 (3). The oxidation of saturated aliphatic hydrocarbons with hydrogen peroxide over titanium silicalites is described in EP-A 376 453 (4).

The synthesis route for preparing propylene oxide starting from propene, hydrogen and oxygen is described in DE-A 44 25 672 (5) and the publications cited in (5). Functionalized zeolites are used as catalysts.

The abovementioned publications (1)–(5) do not mention gauze fabrics as supports. However, gauze catalysts without zeolites are known from other applications as described herein. Furthermore, EP-A 511 739 (6) describes membranes comprising aluminum oxide supports having films of zeolitic crystal bodies applied thereon for use in separation processes. In Microp. Mater. 5 (1995), 245–253 (7), Yamazaki and Tsutsumi describe the preparation and the properties of membranes made of mordenite (zeolite structure) supported on stainless steel or polytetrafluoroethylene. Zeolites supported on copper wire gauzes for use as reduction catalysts in the cleaning of exhaust gases (DeNox) are known from Calis et al., Chem.-Ing.-Tech. 67 (1995), 777–780 (8). However, the zeolites mentioned in (6)–(8) do not contain titanium or vanadium.

Since alkali metal, even if only present in trace amounts, may destroy the catalytic activity of titanium and vanadium zeolites in oxidation reactions, the ways of supporting described in (6)–(8) are unsuitable for the particular purposes of oxidation processes. In (7) and (8), for example, alkali metal-containing zeolite synthesis gels are used as starting materials.

It is an object of the present invention to provide improved catalysts, in particular for the preparation of epoxides from olefins, without the disadvantages of the prior art. In particular, the catalysts should be very easy to produce and highly efficient.

We have found that this object is achieved by a gauze catalyst based on titanium or vanadium zeolites and inert gauze fabrics.

Inert gauze fabrics, ie. gauze supports, especially wire gauzes, are preferably made of metal such as stainless steel, copper, silver, aluminum or nickel or alloys such as brass or kanthal (iron/chromium/aluminum/cobalt), plastic such as polytetrafluoroethylene, aluminum oxide such as α-aluminum oxide, glass fiber, carbon fiber or graphite. It is also possible to use a combination of two or more of the abovementioned gauze fabric materials.

Since alkali metals, even if only present in trace amounts, may destroy the catalytic activity of the titanium and vanadium zeolites in oxidation reactions, the alkali metal content (in particular sodium and/or potassium in this case) is preferably less than 500 ppm, in particular less than 100 ppm, especially less than 40 ppm, in each case based on the weight of the titanium or vanadium zeolites. Alkali metal contents as low as this can be achieved by appropriate preparation methods.

Zeolites are known to be crystalline aluminosilicates having ordered channel and cage structures, whose pore openings are in the micropore region of less than 0.9 nm. The framework of such zeolites is composed of $SiO_4$ and $AlO_4$ tetrahedra joined together via common oxygen bridges. A survey of the known structures may be found for example in W. M. Meier and D. H. Olson, Atlas of Zeolite Structure Types, Butterworth, 2nd Edition, London 1987.

Zeolites which contain no aluminum and in which some of the Si(IV) in the silicate framework has been replaced by titanium as Ti(IV) are also known. These titanium zeolites, in particular those having a crystal structure of the MFI type, and methods for preparing them are described for example in EP-A 311 983 or EP-A 405 978. Apart from silicon and titanium, these materials may also contain additional elements such as aluminum, gallium, boron or small amounts of fluorine.

In the gauze catalyst of the invention, some or all of the titanium of the zeolite may be replaced by vanadium. A molar ratio of titanium and/or vanadium to the sum of silicon and titanium and/or vanadium is usually from 0.01:1 to 0.1:1.

It is known that titanium zeolites having the MFI structure can be identified by particular X-ray diffraction patterns and additionally by a skeletal vibration band in the infrared region at about 960 cm$^{-1}$ and thus differ from alkali metal titanates or crystalline and amorphous $TiO_2$ phases.

The aforementioned titanium and vanadium zeolites are typically prepared by reacting an aqueous mixture of an $SiO_2$ source, a titanium source or vanadium source such as titanium dioxide or a corresponding vanadium oxide and a nitrogen-containing organic base (template compound), for example tetrapropylammonium hydroxide, in a pressure vessel at elevated temperature over a period of several hours or a few days. The crystalline product is filtered off, washed and dried and then calcined at elevated temperature to remove the organic nitrogen base. In the powder thus obtained at least some of the titanium or vanadium is present within the zeolite framework in varying proportions with four-, five- or six-fold coordination. To improve the catalytic properties, the titanium or vanadium zeolite powder may additionally be subjected to repeated wash with a hydrogen peroxide solution acidified with sulfuric acid, after which the titanium or vanadium zeolite powder must be dried and calcined again. The pulverulent titanium zeolite or vanadium zeolite must then in accordance with the invention be finally processed in a shaping operation with additions of suitable inert binder to obtain a handlable catalyst.

The desire to use titanium zeolites of the MFI, BEA, MTW, TON or MOR type as catalysts, however, gives rise to some serious disadvantages.

Processing of the titanium zeolite powders prepared in shaping procedures to produce conventionally handlable catalysts is labor intensive and after an extrusion with or without an inert binder requires a further energy and time intensive drying and calcining step. It is also disadvantageous to apply large zeolite crystals by means of a melt or sinter process. Furthermore, in a fixed bed arrangement of the conventionally shaped titanium zeolites, it is difficult to achieve high catalyst utilization on the one hand and to reduce the pressure drop over the length of the reactor on the other. When conducting oxidations in the gas phase, it is furthermore desirable to employ high gas velocities to be able to avoid consecutive reactions by keeping residence times short. These problems have been solved by the present invention.

Preferred titanium or vanadium zeolites are the titanium or vanadium silicalites having a zeolite structure described in (5), preferably with a pentasil zeolite structure, especially the types with X-ray assignment to an MFI, MEL or MFI/MEL mixed structure. Zeolites of this type are described, for example, in W. M. Meier and D. H. Olson, Atlas of Zeolite Structure Types, Butterworths, 2nd Edition, London 1987. Also conceivable for the present invention are titanium-containing zeolites with a structure of ZSM-48, ZSM-12, ferrierite or β-zeolite and of mordenite.

In another preferred embodiment, the gauze catalyst according to the invention further comprises from 0.01 to 30% by weight, in particular from 0.05 to 15% by weight, especially from 0.1 to 8% by weight, in each case based on the amount of the titanium or vanadium zeolites, of one or more noble metals from the group consisting of gold, silver, rhenium, ruthenium, rhodium, palladium, osmium, iridium and platinum. It is particularly preferred to include the aforementioned noble metals in the aforementioned amounts when using titanium or vanadium silicalites having zeolite structure.

In the present invention, titanium or vanadium zeolites, if desired in combination with noble metals or noble metal-containing compounds, are crystallized onto an inert gauze fabric, preferably by contacting, in a hydrothermal reaction, an $SiO_2$ source with a titanium or vanadium component in the presence of diluted aqueous solutions of tetraalkylammonium halides with addition of ammonia or tetraalkylammonium hydroxides. The process of the invention makes it possible to obtain the resulting titanium or vanadium zeolite crystals in high yield and directly in the form of platelet-like, alkali metal-free primary crystallites. Titanium silicate zeolites of the structure type MFI, MEL, MTW, BEA, TON or MOR are preferably obtained according to the process of the invention by adding the titanium component in the form of a soluble, aqueous or aqueous-alcoholic titanium compound in the aforementioned manner during the hydrothermal conversion of the reaction mixture.

Furthermore, the novel alkali metal-free preparation process for gauze catalysts makes it possible that the material is present on the gauze fabrics directly and without additional ion exchange in the catalytically active form after heat treatment at from 350 to 600° C., preferably at from 400 to 550° C., in particular at from 450 to 500° C.

The gauze catalysts of the invention comprise catalytically active material, ie. titanium or vanadium zeolites with or without noble metals, of usually from 1 to 30% by weight, in particular from 5 to 20% by weight.

The titanium or vanadium zeolite-coated gauze fabrics may in turn be shaped into monoliths directly and ideally adapated to the reactor geometry by conventional methods.

The gauze catalysts of the invention may also be used advantageously when heat of reaction is to be added or dissipated via the gauze catalyst body, which has good conductivity and is made, for example, of metal, or when, in a flow reactor, the monolithic gauze packing is to have the additional function of acting as a static mixer or is to ensure a very small pressure drop over the length of the reactor at high gas velocities in the gas phase.

It is particularly easy to prepare the present gauze catalysts of the invention since the inert carriers are usually already converted into the gauze catalysts of the invention during the crystallization of the titanium or vanadium zeolites.

Gauze catalysts based on titanium or vanadium zeolites and inert gauze fabrics according to the invention are very useful for accelerating oxidation reactions. Oxidation reactions are in particular epoxidations of olefinic double bonds, the oxidation of hydrogen to give hydrogen peroxide, ammoxidation reactions and hydroxylations, for example of aromatics to give phenols.

Accordingly, the present invention also provides a process for preparing epoxides from olefins using oxygen or oxygen-generating compounds, where the olefins are converted in the presence of the novel gauze catalysts based on titanium or vanadium zeolites and inert gauze fabrics.

The epoxidation of the invention may be conducted in the liquid phase, in the gas phase or in the supercritical phase, depending on the olefin to be converted and the oxygen source. For example, epoxidations using aqueous hydrogen peroxide are advantageously conducted in the liquid phase, while the conversion of the olefins, for example using a hydrogen/oxygen gas mixture, can be effected in the liquid phase or in the gas phase.

If the epoxidation is conducted, for example, using aqueous hydrogen peroxide, eg. 10–50% strength by weight aqueous hydrogen peroxide, as oxygen-generating compound, excellent results are obtained using the novel gauze catalysts based on titanium or vanadium zeolites alone, without any nobel metal content. If, on the other hand, for example a hydrogen/oxygen gas mixture is used as oxygen source, it is advisable in many cases to incorporate the aforementioned nobel metals in the gauze catalysts of the invention, particular preference being given to nobel metal-containing gauze catalysts containing titanium or vanadium silicalites having zeolite structure.

The epoxidation of the invention in the liquid phase is advantageously conducted at a pressure of from 1 to 10 bar and in the presence of solvents. Suitable solvents include alcohols, eg. methanol, ethanol, isopropanol or tert-butanol or mixtures thereof and especially water. It is also possible to use mixtures of the aforementioned alcohols with water. In certain cases, the use of water or aqueous solvent systems causes a significant selectivity increase of the desired epoxide compared to using pure alcohols as solvent.

The epoxidation of the invention is usually conducted at from –20 to 70° C., in particular at from –5 to 50° C. If a hydrogen/oxygen gas mixture is used, the molar ratio of hydrogen to oxygen can usually be varied from 1:10 to 1:1 and is particularly favorably from 1:5 to 1:1. The molar ratio of oxygen to olefin is usually from 1:4 to 1:10, preferably from 1:5 to 1:7. Any inert gas may be added as carrier gas, nitrogen being particularly suitable.

The olefin used may be any organic compound containing at least one ethylenically unsaturated double bond. The compound may be aliphatic, aromatic or cycloaliphatic and may be linear or branched. The olefin preferably contains from 2 to 30 carbon atoms. More than one ethylenically unsaturated double bond may be present, as in dienes or trienes. The olefin may additionally contain functional group [sic] such as halogen, carboxyl, carboxylic ester, hydroxyl, ether linkages, sulfide linkages, carbonyl, cyano, nitro or amino.

Typical examples of such olefins include ethylene, propene, 1-butene, cis- and trans-2-butene, 1,3-butadiene, pentenes, isoprene, hexenes, octenes, nonenes, decenes, undecenes, dodecenes, cyclopentene, cyclohexene, dicyclopentadiene, methylenecyclopropane, vinylcyclohexane, vinylcyclohexene, allyl chloride, acrylic acid, methacrylic acid, crotonic acid, vinylacetic acid, allyl alcohol, alkyl acrylates, alkyl methacrylates, oleic acid, linoleic acid, linolenic acid, esters and glycerides of such unsaturated fatty acids, styrene, α-methylstyrene, divinylbenzene, indene and stilbene. Mixtures of the aforementioned olefins can also be epoxidized according to the process of the invention.

The process of the invention is particularly useful for the epoxidation of propene to give propylene oxide.

The present invention also provides a process for preparing hydrogen peroxide from hydrogen and oxygen, where the reaction is conducted using the novel gauze catalysts based on titanium or vanadium zeolites and inert gauze fabrics, usually in a heterogeneously catalyzed reaction. Excellent results are in particular obtained using gauze catalysts comprising titanium or vanadium silicalites having zeolite structure and preferably also from 0.01 to 30% by weight, based on the amount of the titanium or vanadium silicalites, of one or more of the aforementioned noble metals.

The present invention further provides a process for preparing hydroxylamines from ammonia or the corresponding amines, hydrogen and oxygen, where the reaction is conducted in the presence of gauze catalysts based on titanium or vanadium zeolites and inert gauze fabrics. Excellent results are in particular obtained using gauze catalysts comprising titanium or vanadium silicalites having zeolite structure and preferably also from 0.01 to 30% by weight, based on the amount of the titanium or vanadium silicalites, of one or more of the aforementioned noble metals.

The gauze catalyst of the invention is particularly useful for preparing unsubstituted hydroxylamine, but also for preparing substituted hydroxylamines from the corresponding amine, hydrogen and oxygen, for example from cyclic or aliphatic amines such as cyclohexylamine, some of which may undergo further reaction to give the corresponding lactams under the reaction conditions.

The preparation of hydroxylamines in the liquid phase is advantageously conducted at a pressure of from 1 to 100 bar and in the presence of solvents. Suitable solvents are alcohols, eg. methanol, ethanol, isopropanol or tert-butanol or mixtures thereof and especially water. It is also possible to use mixtures of the aforementioned alcohols with water. In certain cases, the use of water or aqueous solvent systems causes a significant selectivity increase of the desired product compared to using pure alcohols as solvent.

The conversion to the desired hydroxylamines according to the invention is usually carried out at from −5 to 70° C., in particular at from 20 to 50° C. The molar ratio of hydrogen to oxygen may usually be varied from 1:10 to 1:1 and is particularly advantageously from 1:2.5 to 1:1. The molar ratio of oxygen to ammonia is usually from 1:1 to 1:3, preferably from 1:1.5 to 1:1.7. Any inert gas may be added as carrier gas, nitrogen being particularly suitable.

The examples below illustrate the novel preparation process for the gauze catalysts described and the catalytic properties of the novel gauze catalysts without limiting the scope of the invention.

EXAMPLE 1

This example describes the preparation of a gauze catalyst of the invention using stainless steel gauzes as support material.

329 g of deionized water were charged initially to a stirred flask and 22.7 g of tetraisopropyl orthotitanate were added dropwise with stirring over half an hour. The white suspension was cooled down to 5° C. Then 272 g of hydrogen peroxide solution (30% by weight in water) were added to form a reddish orange solution, which was stirred for 39 minutes. Then 704 g of ammonia solution (25% by weight in water) were added to form a yellow suspension which was held at room temperature for 15 hours. The reaction was finally heated to 80° C. for 3 hours to decompose excess hydrogen peroxide.

58.8 g of tetrapropylammonium bromide, 88.7 g of silica (Aerosil® 200, Degussa), 122.4 g of deionized water and 626 g of the aforementioned titanate hydrolysate suspension were homogenized in a polypropylene cup.

Two gauze pieces of 10.8 g and 11.9 g of stainless steel wire gauze (steel 1.4401) were introduced into an autoclave cup lined with Teflon and filled up with 150 g of the above titanium zeolite synthesis batch. This mixture was crystallized at 175° C. over 168 hours.

After the crystallization had ended, the gauzes were removed, washed neutral with water, dried at 120° C. and calcined at 500° C. under synthetic air (3% by volume of oxygen, 97% by volume of nitrogen). Loosely adhering residual gel was removed by means of a pressurized air jet. The weight gain of the two pieces owing to titanium zeolite crystallized thereon was 8.7 and 8.0% by weight, respectively. These gauzes were used in the propylene oxide production of Example 3 without further pretreatment.

COMPARATIVE EXAMPLE A

This comparative example describes the preparation of a titanium silicalite with MFI structure in accordance with the state of the art as represented in EP 376 453 (4).

30 ml of tetraethyl orthotitanate were added dropwise with stirring (300 rpm) over 15 minutes to 375 ml of deionized water previously cooled down to 2° C. Then 360 ml of a cold hydrogen peroxide solution (30% by weight in water) were added to form a reddish orange solution, which was stirred for 2 hours. Then 625 ml of an aqueous tetrapropylammonium hydroxide solution (20% by weight in water) were added, followed after an hour by 100 g of a colloidal silicasol solution (40% by weight of $SiO_2$, Ludox® AS-40, Du Pont). This mixture was stored overnight at room temperature, heated the next day at 80° C. with stirring (300 rpm) for 7 hours, introduced into a 2 l capacity stirred pressure vessel and reacted at 175° C. for 240 hours.

The cold reaction mixture was filtered, the filter cake was repeatedly washed neutral with deionized water, dried overnight at 120° C. and then calcined at 550° C. in air. Based on starting $SiO_2$, the yield of titanium silicalite was 93%. According to the X-ray diffraction pattern, it was a pure titanium silicalite having MFI structure.

EXAMPLE 2

This example describes the preparation of a gauze catalyst of the invention using graphite gauzes as support material.

329 g of deionized water were charged initially to a stirred flask and 22.7 g of tetraisopropyl orthotitanate were added dropwise with stirring over half an hour. The white suspension was cooled down to 5° C. Then 272 g of hydrogen peroxide solution (30% by weight in water) were added to form a reddish orange solution, which was stirred for 30 minutes. Then 704 g of ammonia solution (25% by weight in water) were added to form a yellow suspension which was held at room temperature for 15 hours. The reaction was finally heated to 80° C. for 3 hours to decompose excess hydrogen peroxide.

58.8 g of tetrapropylammonium bromide, 88.7 g of silica (Aerosil® 200, Degussa), 122.4 g of deionized water and 626 g of the aforementioned titanate hydrolysate suspension were homogenized in a polypropylene cup.

Two gauze pieces of 5.2 g and 5.3 g of a graphite fabric gauze (KDL 8042, 200 g/m$^2$) were introduced into an autoclave cup lined with Teflon and filled up with 150 g of the above titanium zeolite synthesis batch. This mixture was crystallized at 175° C. over 168 hours.

After the crystallization had ended, the gauzes were removed, washed neutral with water, dried at 120° C. and calcined at 500° C. under nitrogen. Loosely adhering residual gel was removed by means of a pressurized air jet. The weight gain of the two pieces owing to titanium zeolite crystallized thereon was 10.4 and 8.7% by weight, respectively. These gauzes were used in the propylene oxide production of Example 4 without further pretreatment.

COMPARATIVE EXAMPLES B AND C

These synthesis examples describe the effect obtained on switching from tetrapropylammonium hydroxide to tetrapropylammonium bromide while at the same time using ammonia solution.

In a glass flask equipped with a stirrer and reflux condenser, 45.1 g of deionized water were cooled down to 5° C. 6.9 g of tetraisopropyl orthotitanate and 81.4 g of hydrogen peroxide solution (30% by weight in water) were added dropwise in the course of 15 minutes. To the resulting reddish orange solution was added 211.0 g of an ammonia solution (25% by weight in water), and the resulting batch was left to warm up overnight to room temperature. Finally, it was heated over 3 hours to 80° C. with stirring. Any weight loss was compensated by addition of a corresponding amount of ammonia solution.

Of this solution thus prepared, 156.8 g were mixed with 56.0 g of tetrapropylammonium hydroxide solution (20% by weight in water) and 52.8 g of Ludox® AS-40 silicasol (Du Pont) in the course of 3 minutes, and the mixture was introduced into a Teflon-lined autoclave vessel and sealed in pressure tight. This batch will hereinafter be referred to as batch B.

A further 156.5 g of the solution prepared at the beginning were mixed with 14.7 g of tetrapropylammonium bromide in 44.8 g of water and 53.1 g of Ludox® AS-40 silicasol (Du Pont) in the course of 3 minutes, and the mixture was introduced into a Teflon-lined autoclave vessel and sealed in pressure tight. This batch will hereinafter be referred to as batch C.

Batches B and C were each reacted at from 183 to 185° C. over 192 hours. The crystalline reaction products were filtered off, washed neutral, dried and calcined in air at 500° C. in the course of 5 hours. The properties of the two comparative examples are compared in the following table.

| Batch | Yield | Si/Ti [molar] | Potassium [% by weight] | Size [μm] | Shape |
|---|---|---|---|---|---|
| B | 96% | 36 | 0.001 | 0.1 | globular |
| C | 95% | 36 | 0.001 | 26 | platelet-like |

EXAMPLE 3

This example describes the production of propylene oxide according to the invention using the catalyst of Example 1.

9 g of catalyst gauze from Example 1 were suspended in 45 ml of methanol in a glass pressure autoclave. The autoclave was cooled down to −30° C., pressurized with 20.5 g of propene and then heated to 0° C. Then 30 g of a 30% strength by weight aqueous H$_2$O$_2$ solution was added over 20 minutes and the reaction mixture was stirred at 0° C. for a further 5 h. After the reaction had ended, the amount of dissolved propylene oxide was determined by gas chromatography. 1.65% by weight of propylene oxide were found.

EXAMPLE 4

This example describes the production of propylene oxide according to the invention using the catalyst of Example 2.

15 g of catalyst gauze from Example 2 were suspended in 45 ml of methanol in a glass pressure autoclave. The autoclave was cooled down to −30° C., pressurized with 19.7 g of propene and heated to 0° C. Then 40.6 g of a 30% strength by weight aqueous H$_2$O$_2$ solution was added over 25 minutes and the reaction mixture was stirred at 0° C. for a further 5 h. After the reaction had ended, the amount of dissolved propylene oxide determined by gas chromatography was 4.9% by weight.

The Examples 1–4 show that the gauze catalysts of the invention are easier to prepare and give better results in the epoxidation than titanium zeolites supported conventionally in a multistage process as described in Comparative Examples B–E (see below).

COMPARATIVE EXAMPLE D

This example describes the production of propylene oxide using unshaped catalyst of Comparative Example B.

1.5 g of a catalyst from Comparative Example B were suspended in 45 ml of methanol in a glass pressure autoclave. The autoclave was cooled down to −30° C., pressurized with 23.5 g of propene and heated to 0° C. 28.9 g of a 30% strength by weight aqueous H$_2$O$_2$ solution was then added over 20 minutes and the reaction mixture was stirred at 0° C. for a further 5 h. After the reaction had ended, the amount of dissolved propylene oxide determined by gas chromatography was 3.7% by weight.

COMPARATIVE EXAMPLE E

This example describes the production of propylene oxide using shaped catalyst of Comparative Example B.

100 g of the catalyst from Comparative Example B were combined with 12.5 g of Ludox® AS-40, 5 g of methylcellulose and 70 ml of water and compacted for 120 minutes in a kneader and then shaped to extrudates having a diameter of 2 mm. The extrudates were dried overnight at 110° C. and calcined at 500° C. for 5 h. The extrudates thus obtained were processed to give chips (particle size about 1 mm).

1.5 g of these catalyst chips were suspended in 45 ml of methanol in a glass pressure autoclave. The autoclave was cooled down to −30° C., pressurized with 29.7 g of propene and heated to 0° C. Then 31 g of a 30% strength by weight aqueous H$_2$O$_2$ solution was added over 20 minutes and the reaction mixture was stirred for further 5 h. After the reaction had ended, the amount of dissolved propylene oxide was determined by gas chromatography. 2.6% by weight of propylene oxide were found.

This indicates that shaping significantly reduces the catalytic activity of the starting material (see Comparative Example D containing 3.7% by weight of propylene oxide).

We claim:

1. A gauze catalyst comprising a titanium framework zeolite having a MPI, MEL, BEA, MTW, TON, MOR structure or an MFI/MEL mixed structure, and an inert gauze fabric.

2. A gauze catalyst as claimed in claim 1, wherein the inert gauze fabric is made of metal, plastic, aluminum oxide, glass fiber, carbon fiber and/or graphite.

3. A gauze catalyst as claimed in claim 1, wherein the titanium framework zeolite has an alkali metal content of less than 500 ppm, based on the weight of the titanium framework zeolite.

4. A gauze catalyst as claimed in claim 1, wherein the titanium framework zeolite is a titanium silicalite having a zeolite structure.

5. A gauze catalyst as claimed in claim 4, further comprising from 0.01 to 30% by weight, based on the amount of the titanium silicalite having a zeolite structure, of one or more noble metals selected from the group consisting of gold, silver, rhenium, ruthenium, rhodium, palladium, osmium, iridium and platinum.

6. A gauze catalyst as claimed in claim 1, further comprising from 0.01 to 30% by weight, based on the amount of the titanium framework zeolite, of one or more noble metals selected from the group consisting of gold, silver, rhenium, ruthenium, rhodium, palladium, osmium, iridium and platinum.

7. A process for preparing a gauze catalyst as claimed in claim 1, which comprises crystallizing a titanium framework zeolite and, optionally, a noble metal or noble metal-containing compound, onto an inert gauze fabric.

8. A process for preparing an epoxide, comprising reacting oxygen or an oxygen-generating compound with an the olefin in the presence of the gauze catalyst of claim 1.

9. The process of claim 8, wherein the olefin is propylene.

10. A process for preparing hydrogen peroxide, comprising reacting hydrogen and oxygen in the presence of the gauze catalyst of claim 1.

11. A process for preparing a hydroxylamine, comprising reacting ammonia or an amine, hydrogen and oxygen, in the presence of the gauze catalyst of claim 1.

* * * * *